(12) United States Patent
Heath et al.

(10) Patent No.: US 6,366,719 B1
(45) Date of Patent: Apr. 2, 2002

(54) PHOTODYNAMIC THERAPY LIGHT DIFFUSER

(75) Inventors: Ross Heath, Santa Barbara; Mark Purter, Lompoc; Patrick Stephens, Santa Rosa, all of CA (US)

(73) Assignee: Miravant Systems, Inc., Santa Barbara, CA (US)

( * ) Notice: Subject to any disclaimer, the term of this patent is extended or adjusted under 35 U.S.C. 154(b) by 0 days.

(21) Appl. No.: 09/640,944

(22) Filed: Aug. 17, 2000

(51) Int. Cl.⁷ .................................................. G02B 6/42
(52) U.S. Cl. ........................ 385/31; 385/901; 385/147; 606/15
(58) Field of Search .............................. 385/31, 33, 115, 385/133, 116, 147, 24, 901; 606/15, 16, 17; 362/551, 552, 556

(56) References Cited

U.S. PATENT DOCUMENTS

| | | | |
|---|---|---|---|
| 5,042,980 A | 8/1991 | Baker et al. | 606/7 |
| 5,196,005 A | 3/1993 | Doiron et al. | 606/7 |
| 5,303,324 A | 4/1994 | Lundahl | 385/147 |
| 5,373,571 A | * 12/1994 | Reid et al. | 385/31 |
| 5,536,265 A | 7/1996 | Van Den Bergh et al. | 606/2 |
| 5,695,583 A | 12/1997 | Van den Bergh et al. | 156/153 |

OTHER PUBLICATIONS

Ed Sinofsky, Ph. D. "High Power Diffusing Tip Fibers for Photocoagulation" Leos 96., IEEE, vol. 1, 1994 p. 263 vol. 1.*

Jan. 14, 1999, Tan et al., Photodynamic therapy using 5–aminolaevulinic acide for oesophageal adenocarcinoma associated with Barrett's metaplasia, J. Photochem. Photobiol. B: Biol. 5 3 (1999) 75–80.

Feb. 1984, H. Fujii et al., Light scattering properties of a rough–ended optical fibre, Optics and Laser Technology, 40–44.

* cited by examiner

Primary Examiner—Phan T. H. Palmer
(74) Attorney, Agent, or Firm—Bryan Cave LLP

(57) ABSTRACT

An optical light diffuser providing a generally cylindrical pattern of light emission. The diffuser is formed from an optical fiber operable to transmit the optical radiation from its proximal end to its distal end and having a guiding core and a cladding surrounding the core. The optical fiber has an abraded section at its distal end that allows light to escape uniformly over the abraded section forming a generally cylindrical pattern of diffuse light that surrounds the distal end of the optical fiber.

10 Claims, 1 Drawing Sheet

PHOTODYNAMIC THERAPY LIGHT DIFFUSER

FIELD OF THE INVENTION

The present invention relates generally to optical devices and, more particularly, to a fiberoptic diffuser providing a generally cylindrical pattern of light emission.

BACKGROUND OF THE INVENTION

Light-based treatments (i.e., phototherapy) of many kinds are being used or considered for addressing a number of medical ailments. Phototherapy of diseased tissue includes various forms of treatment including photoablation, photodynamic therapy, or photocoagulation. In each of these, control of the treatment outcome relies on control of the dosage of light administered, as well as the dosage of any additional agents such as photosensitizers used in conjunction with the therapeutic light.

Photodynamic therapy (PDT) is an evolving treatment that employs the interaction between photoactive drugs and light of an appropriate wavelength to destroy diseased or malignant tissue. During a PDT procedure, one or more photosensitive molecules are administered within a target tissue of a patient and are then illuminated with phototherapeutic light having a wavelength operable for interacting with the photosensitive molecules in such a manner as to produce a photoactivated species of the molecules possessing therapeutic properties. The photoactivated species that are formed either destroy cells or arrest physiological activity in the associated diseased tissue thereby effecting a treatment of the target tissue.

In PDT procedures, as well as in certain other biomedical applications, optical waveguides (referred to herein as "optical fibers") are used to deliver the therapeutic light energy to internal areas of the human body not readily accessed directly by the light source. In a number of these medical applications, it is necessary to deliver a uniform, cylindrical pattern of light as in the irradiation of a cylindrical area of a blood vessel. Optical fibers used in such therapies typically consist of an inner core having one index of refraction, surrounded by a cladding having a slightly lower index of refraction. Both the core and cladding may be comprised of either an optical glass or polymeric material (such as plastic). Light propagates down the optical fiber by means of total internal reflection at the interface between the inner core and the cladding. The optical fiber is terminated at its distal end with a diffuser having an irradiance distribution appropriate to the particular treatment protocol. An outer protective jacket often covers the optical fiber. Alternatively, light can be delivered into the body using an optical waveguide that consists of a core region only and the waveguiding effect is provided by the interface between the core and the surrounding medium. This type of optical waveguide will also be referred to herein as an optical fiber.

There are various methods used to produce the desired output profiles from interstitial to intraluminal uses. One such device consists of a terminating optical fiber with an attachment on its distal end that forms the diffusing section of the device. Such devices include those described in Dorion et al. U.S. Pat. No. 5,196,005 and Lundahl U.S. Pat. No. 5,303,324. Another type of device consists of an optical fiber with is modified on the distal end. For example, in Fujii et al., *Light Scattering Properties of a Rough-ended Optical Fiber, Optics and Laser Technology*, February 1984, a process for creating uniform wide-angle irradiation of a laser beam by chemically roughening the output end of a glass fiber is disclosed. In similar processes, the glass core of an optical fiber is stripped by removing the jacket and cladding and then chemically etching the core to distribute the light into layers containing scattering particles to create a uniform cylindrical pattern.

One current approach to diffuser construction is to diffuse scattering elements in a clear material such as epoxy, often with a density gradient of scattering elements to achieve an irradiance pattern that is uniform along the length of the diffuser. One drawback of this approach is that the diffuser is constructed separately and then attached to the end of the fiber resulting in a difficult manufacturing process. Another drawback is that it is difficult to shape the irradiance pattern significantly because it is difficult to arrange the scattering elements in a systematic manner. Further, this technique often results in a fiber optic diffuser with a maximum diameter that is greater than the diameter of the fiber.

Another current approach to diffuser construction is to modify the fiber itself to prevent the total internal reflection of light at the core-cladding interface. There are several ways this is accomplished. One way is to choose a ratio of the indices of refraction between the outer cladding and the core region of the optical fiber so that internal reflection within the core region is substantially less than total. This causes light to radiate outward through the side of the core region and to emerge through (a preferably transparent) cladding. Another way is to alter the interface between the fiber optic core and cladding to increase side radiation. Texturing the outer surface of the core region to provide a ground glass effect is one method commonly used. Another is to position or embed light scattering elements such as tiny particles at the surface of the fiber optic core near the interface with the cladding. Light scattering particles can also be imbedded throughout the cladding to enhance the side delivery of radiation. Yet another approach is to melt or otherwise deform the distal end of the fiber to reduce the waveguiding effect and thereby allow light to be emitted along the deformed region.

Current approaches that modify the fiber itself have only a limited capability to tailor the irradiance distribution. Diffusers which rely on mechanical alteration of the core-to-cladding interface or use a deformed distal end also have the drawback of potentially weakening the mechanical properties of the fiber.

Accordingly, there is a continuing need for an improved optical light diffuser that provides a generally cylindrical pattern of light emission. Desirably, the optical light diffuser would be fabricated relatively readily and would be reliable in operation. In addition, length of the cylindrical pattern of light emanating from the improved optical light diffuser would be varied by facile variation of the manufacturing process.

SUMMARY OF THE INVENTION

The present invention provides an economical and easily manufactured optical light diffuser that generates a generally cylindrical pattern of light emission that may be used in various medical applications, such as photodynamic and photochemical treatments requiring uniform irradiation of internal tissues.

In accordance with the present invention, an optical light diffuser, which can generate a generally cylindrical patter of light emission, is provided. The optical light diffuser preferably consists of an optical fiber having a proximal end for connection with an optical light source and a distal end, gradually tapered and preferably terminating in a bullet-shaped tip. The surface of the fiber at the distal end is mechanically abraded in a manner that allows light to escape uniformly over the desired length of the diffuser forming a generally tailored cylindrical pattern of diffuse light.

BRIEF DESCRIPTION OF THE DRAWINGS

To facilitate further discussion of the invention.

DETAILED DESCRIPTION OF THE INVENTION

Figure 1:
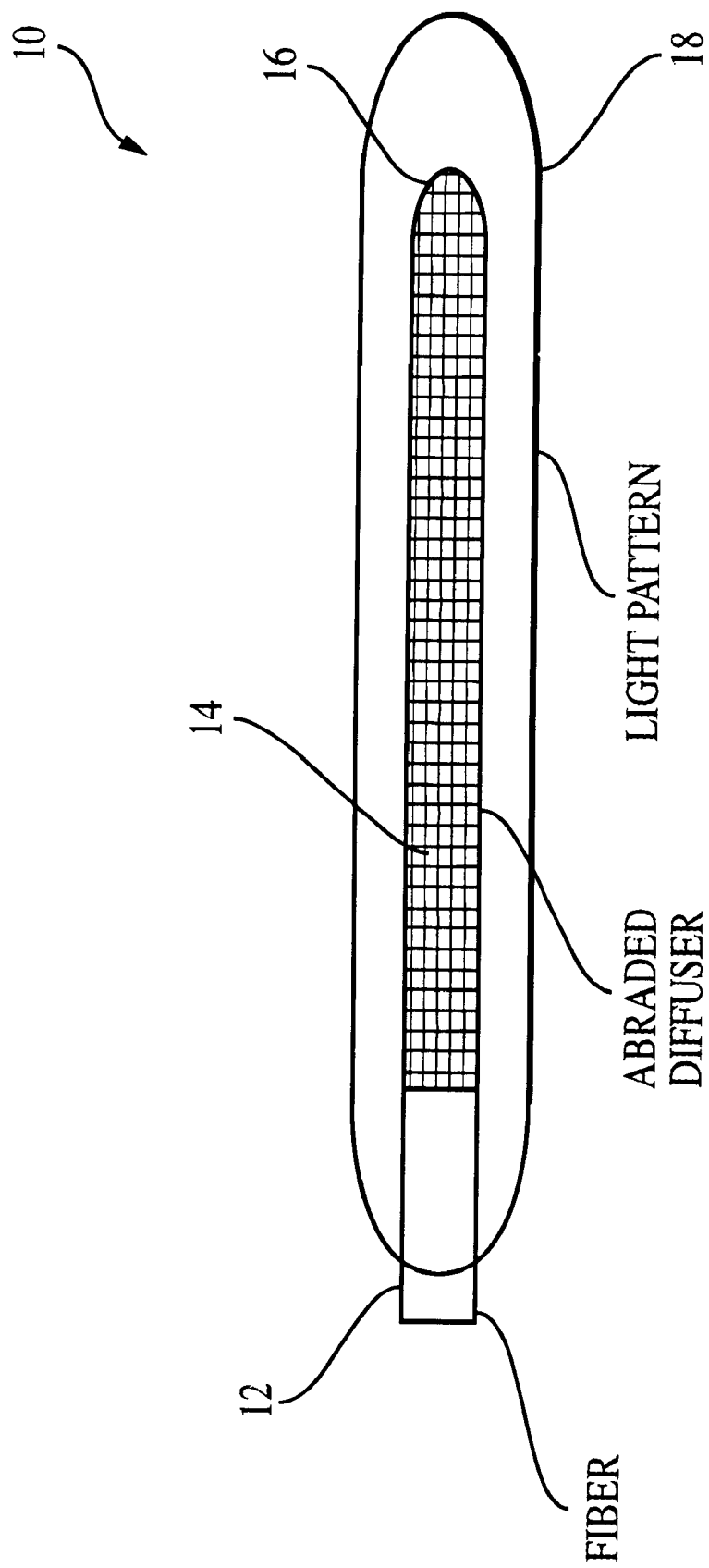
FIG. 1 is a longitudinal view of the optical light diffuser of the present invention. This drawing is for illustrative purposes only and should not be used to unduly limit the scope of the claims.

FIG. 1 illustrates an embodiment of the optical light diffuser 10 of the present invention. The optical light diffuser 10 is formed from an optical fiber 12 capable of transmitting therapeutic light. One preferred optical fiber 12 comprises a fused silica core (capable of transmitting light of wavelengths in the range of 300–1,100 nm), surrounded by a silica cladding. The core may be sized to be in the range of 100–1,500 microns in diameter, and the cladding may be 5–60 microns thick. Of course, those skilled in the art will appreciate that other materials and sizes may be used for the optical fiber 12 and are within the scope of the present invention. Such alternative materials include transparent glass, polymers (such as plastic), or any other suitable medium capable of transmitting light, including non-hollow optical waveguides. The light delivery optical fiber 12 may also include a jacket or buffer to strengthen the fiber 12, such as a thin, chemically bonded, polyimide coating.

The length of the optical fiber 12 is chosen so that its distal end can be positioned near or in a desired, remote target tissue (e.g., in vivo) with its proximal end extending out of the patient for connection to a source of optical radiation. The optical fiber 12 must be able to accept optical radiation at its proximal end and transmit most of such received optical radiation to its distal end. Light traveling through the optical fiber generally emerges from the distal end and illuminates surrounding target tissue, resulting in subsequent absorption and scattering of the light by the tissue. When the optical light diffuser 10 is used in conjunction with a PDT procedure, the treatment light delivered by the optical fiber 12 may initiate the chemical reaction of photosensitizers previously injected or absorbed into the target tissue.

The distal end of the optical fiber 12 has an abraded section 14, which may be formed by abrading the optical fiber 12 to disrupt the cladding and the core of the optical fiber 12. The abrasion of the optical fiber 12 starts in the cladding at the proximal end of the abraded section 14 and gradually increases in depth of penetration through the cladding and into the core of the optical fiber 12 forming a gradual taper ending at a rounded tip 16 of the abraded section 14. Preferably, the rounded tip 16 is bullet-shaped as illustrated in FIG. 1. The depth of penetration varies in accordance with the particular optical fiber 12 used to fabricate the optical light diffuser 10. Thus, in the proximal portion of the abraded section 14, only the cladding is disrupted, while the cladding is completely removed and the core abraded as the distal portion of the abraded section 14 (and the optical fiber 12) terminates.

The abraded section 14 may be formed using several different techniques. For example, one technique involves hand sanding the distal portion of an optical fiber 12 to create the abraded section 14. The hand sanding may be accomplished using sandpaper suitable for optical polishing. The optical fiber 12 is preferably hand sanded until the abraded section allows light to escape uniformly over the desired length of the optical fiber 12 forming a substantially cylindrical pattern of diffuse light 18. The hand sanding process may create the abraded section 14 by forming lengthwise (along the axis of the fiber 12) and cross-wise (in the cross-axial direction) grooves in the distal end of the optical fiber 12. One preferred approach is to start the hand sanding process at the distal end of the abraded section 14 forming the bullet-shaped tip and sand until light begins to diffuse (i.e., escape) outwardly from the optical fiber 12. The sanding process then proceeds toward the proximal end of the abraded section 14 to reduce the emission of light from the distal end of the optical fiber 12 until a uniform distribution of light is created. A source of optical light may be coupled to the proximal end of the optical fiber 12 during fabrication to shine optical light through the fiber during the abrasion process. In addition, conventional instrumentation, e.g., a laser beam analyzer and profiler may be employed to check the uniformity of the light pattern diffused from the light diffuser 10. Preferably, the fabrication process results in an optical diffuser having an abraded section that emits light having a generally tailored cylindrical pattern.

The abraded section 14 of the optical diffuser 10 may vary in length in accordance with the desired application. Diffusers exceeding 20 cm in length and having good uniformity of light emission have been produced using the novel method. It has also been discovered that creating a rounded, bullet-shaped tip 16 is crucial to producing a light diffuser 10 having a substantially cylindrical pattern of diffuse light.

In use, the distal portion of the optical diffuser 10 is placed interstitially within a patient near or in a target tissue of interest. If the optical diffuser is used in conjunction with a PDT procedure, the patient likely previously received a dosage of an appropriate photosensitizing agent such as hematoporphyrin derivative (HpD), which is activated at 633 nm, tin ethyl etiopurpurin (SnET2), a second-generation photosensitizer maximally activated at 665 nm, or any other photosensitizer used in PDT treatments including purpurins, chlorins and phthalocyanines. A source of optical radiation generating the treatment light is coupled to the proximal end of the optical fiber 12. For example, a helium-neon (HeNe) laser, a diode laser, an argon-dye laser, or any other suitable light source capable of producing red light at a wavelength appropriate to activate the selected photosensitizers is attached using appropriate couplers to the proximal end of the light delivery optical fiber 12. The light from the laser may be coupled and focused into the proximal end of the light delivery optical fiber 12 using, for example, a conventional SMA lens adapter and fiber termination assembly. The application of therapeutic light to the target tissue will activate the photosensitizing agent within the target tissue giving rise to toxic species of oxygen and other chemical radicals and initiate cellular necrosis.

The present invention provides an inexpensive device for use in photodynamic and photochemical applications that require light administration for drug activation. The device provides for an adjustable (interstitial vs. intraluminal) uniform cylindrical diffuser capable of light diffusion. Because of the flexibility of certain materials that may be used to fabricate the optical fiber 12, the ease of manufacture and the ability to tailor the diffuser length, this device is readily adaptable to many applications. The monolithic construction eliminates problems that often occur at the mechanical interface between fiber and diffuser. Additional benefits from the monolithic construction are ease of tracking and the ability to maintain uniform light output while the optical diffuser is bent while progressing through a tight radius. The characteristics of the optical light diffuser of the present invention make it suitable for use in many photodynamic treatments such as restenosis for inhibition of intimal hyperplasia due to coronary angioplasty, as well as various oncology applications, such as diseases involving the esophagus and lung.

Although the present invention has been described in considerable detail with reference to certain preferred versions thereof, other versions are possible without departing from the spirit and scope of the present invention. Therefore the scope of the appended claims should not be limited to the description of the preferred embodiments described herein. For example, the optical light diffuser of the present invention is suitable for many photodynamic treatments such as restenosis for inhibition of intimal hyperplasia due to coronary angioplasty. In addition, the optical light diffuser may be use in oncology applications, including applications providing light treatment to the esophagus and lung.

What is claimed is:

1. An optical light diffuser providing a generally cylindrical pattern of light emission comprising an optical fiber having a guiding core and a cladding surrounding the core, the optical fiber having a proximal end for coupling to a source of optical radiation and a distal end for emitting optical radiation, the optical fiber being operable to transmit the optical radiation from its proximal end to its distal end, the optical fiber having an abraded section at its distal end that allows light to escape uniformly over the abraded section forming a generally cylindrical pattern of diffuse light that surrounds the distal end of the optical fiber.

2. The optical light diffuser of claim 1 wherein the diameter of the optical fiber over the length of its abraded section tapers into a bullet-shaped tip.

3. The optical light diffuser of claim 1 wherein the light diffuses in a cylindrical radiating pattern with respect to the central axis of the optical fiber.

4. The optical light diffuser of claim 1 wherein the abraded section has a length of up to about 20 cm.

5. The optical light diffuser of claim 1 wherein the abraded section is formed by disrupting the core and the cladding with generally linear grooves in both the axial and cross-axial directions.

6. The optical light diffuser of claim 1 wherein the guiding core is formed from transparent glass or polymer.

7. The optical light diffuser of claim 1 wherein the source of optical radiation generates treatment light and the distal end is placed near to into target tissue, the light delivery optical fiber being operable to transmit the treatment light from its proximal end to its distal end to apply the treatment light to the target tissue.

8. The optical light diffuser of claim 7 wherein the target tissue has been medicated with a photosensitizing agent capable of being activated by the treatment light having a particular wavelength and wherein the source of optical radiation comprises a light source adapted to emit treatment light at the particular wavelength such that the treatment light is partially absorbed by the photosensitizing agent.

9. A method of obtaining controlled light diffusion in a cylindrical pattern from an optical fiber comprising the step of transmitting optical radiation through an optical fiber having an abraded section at its distal end that allows the transmitted optical radiation to escape uniformly over the abraded section forming a generally cylindrical pattern of diffuse light that surrounds the distal end of the optical fiber.

10. The method of claim 10 wherein the diameter of the optical fiber over the length of its abraded section tapers into a bullet-shaped tip.

* * * * *